US012691232B2

(12) United States Patent
Boeschen et al.

(10) Patent No.: US 12,691,232 B2
(45) Date of Patent: Jul. 28, 2026

(54) DEVICE AND PROCEDURE FOR SELF-INJECTION AND INSERTION OF NEEDLES OR CATHETERS INTRAVENOUSLY

(71) Applicant: Sanofi, Paris (FR)

(72) Inventors: Nadja Boeschen, Darmstadt (DE); Hardy Kietzmann, Frankfurt am Main (DE); Horst Mischo, Darmstadt (DE)

(73) Assignee: Sanofi, Paris (FR)

( * ) Notice: Subject to any disclaimer, the term of this patent is extended or adjusted under 35 U.S.C. 154(b) by 414 days.

(21) Appl. No.: 18/572,435

(22) PCT Filed: Jun. 21, 2022

(86) PCT No.: PCT/EP2022/066852
§ 371 (c)(1),
(2) Date: Dec. 20, 2023

(87) PCT Pub. No.: WO2022/268794
PCT Pub. Date: Dec. 29, 2022

(65) Prior Publication Data
US 2024/0285873 A1 Aug. 29, 2024

(30) Foreign Application Priority Data
Jun. 23, 2021 (EP) ..................................... 21315102

(51) Int. Cl.
*A61M 5/42* (2006.01)
*A61B 90/00* (2016.01)
*A61M 5/158* (2006.01)

(52) U.S. Cl.
CPC ............ *A61M 5/427* (2013.01); *A61M 5/158* (2013.01); *A61M 2005/1588* (2013.01);
(Continued)

(58) Field of Classification Search
CPC .................. A61M 5/427; A61M 5/158; A61M 2005/1588; A61M 2205/10;
(Continued)

(56) References Cited

U.S. PATENT DOCUMENTS

2014/0236019 A1 8/2014 Rahum
2015/0065916 A1* 3/2015 Maguire .......... A61B 5/150748
600/573

(Continued)

FOREIGN PATENT DOCUMENTS

WO WO 2022/268794 A1 12/2022

OTHER PUBLICATIONS

International Preliminary Report on Patentability in International Appln. No. PCT/EP2022/066852, mailed on Jan. 4, 2024, 8 pages.
(Continued)

*Primary Examiner* — Jason E Flick
(74) *Attorney, Agent, or Firm* — Fish & Richardson P.C.

(57) ABSTRACT

A self-IV injection device is provided. The self-IV device comprises fixing means to fix the device with respect to an arm of a user, an optical sensor, an IV needle, a drive, and a processor. The self-IV injection device is configured to detect, using the optical sensor, positions of marks placed on the arm of the user, and based on the detected positions of marks placed on the arm of the user, determine, using the processor, a suitable IV injection spot. The self-IV injection device also moves the IV needle, using the drive, to the determined suitable IV injection spot such that the IV needle penetrates a vein of the user.

20 Claims, 3 Drawing Sheets

(52) U.S. Cl.
CPC . *A61M 2205/10* (2013.01); *A61M 2205/3306* (2013.01); *A61M 2205/3327* (2013.01); *A61M 2205/52* (2013.01); *A61M 2205/587* (2013.01); *A61M 2205/6063* (2013.01); *A61M 2205/8206* (2013.01)

(58) Field of Classification Search
CPC .. A61M 2205/3306; A61M 2205/3327; A61M 2205/52; A61M 2205/587; A61M 2205/6063; A61M 2205/8206; A61M 39/02; A61M 2039/0205; A61M 2205/6009; A61B 2090/395
See application file for complete search history.

(56) References Cited

U.S. PATENT DOCUMENTS

| | | | |
|---|---|---|---|
| 2021/0212658 A1* | 7/2021 | McGrath ................ | A61B 8/085 |
| 2022/0409826 A1* | 12/2022 | Arnold ................ | A61M 5/2053 |

OTHER PUBLICATIONS

International Search Report and Written Opinion in International Appln. No. PCT/EP2022/066852, mailed on Sep. 19, 2022, 11 pages.
Needle-based injection systems for medical use Requirements and test methods, Part 1: Needle injection systems, ISO 11608 1:2014(E), Third Edition, Switzerland, ISO, Dec. 15, 2014, pp. 1-13.

* cited by examiner

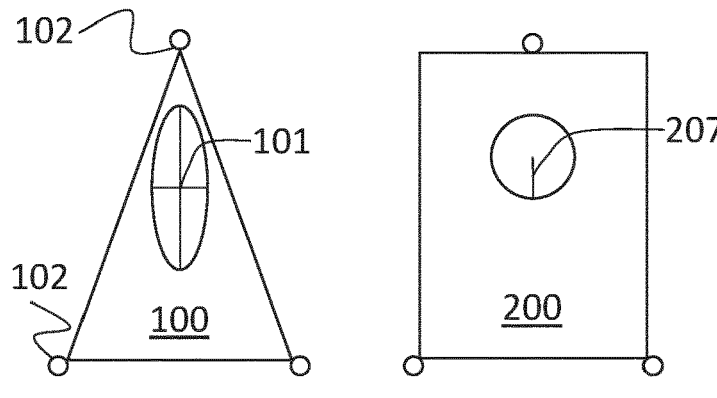
Fig 1a
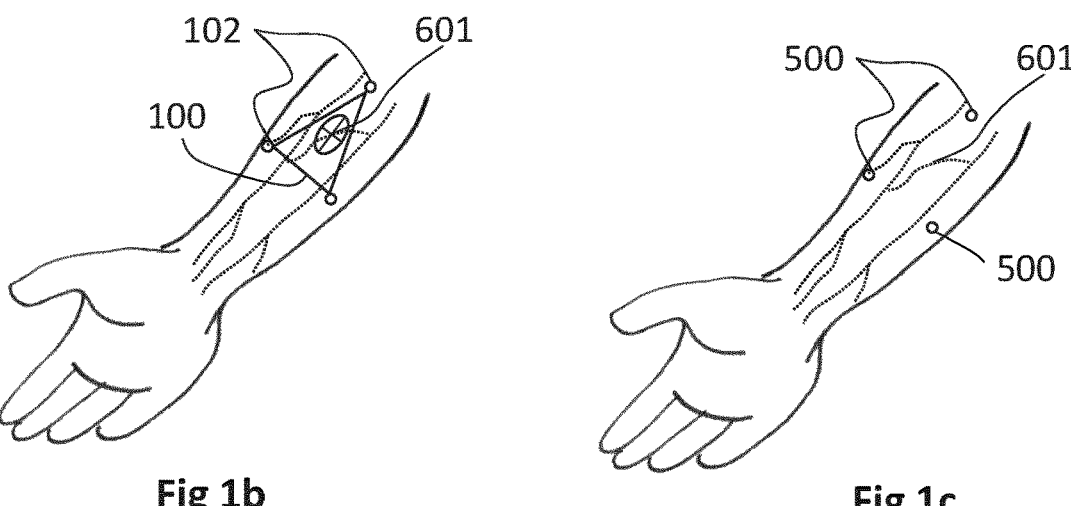
Fig 1b
Fig 1c
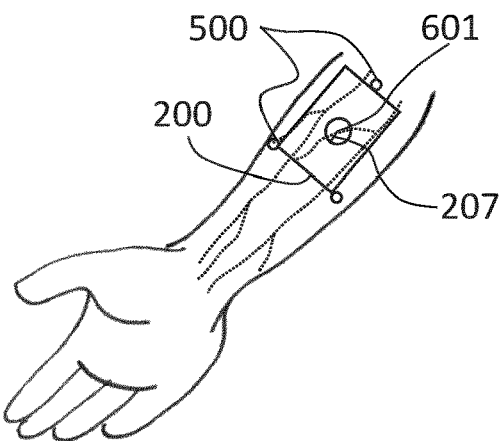
Fig 1d

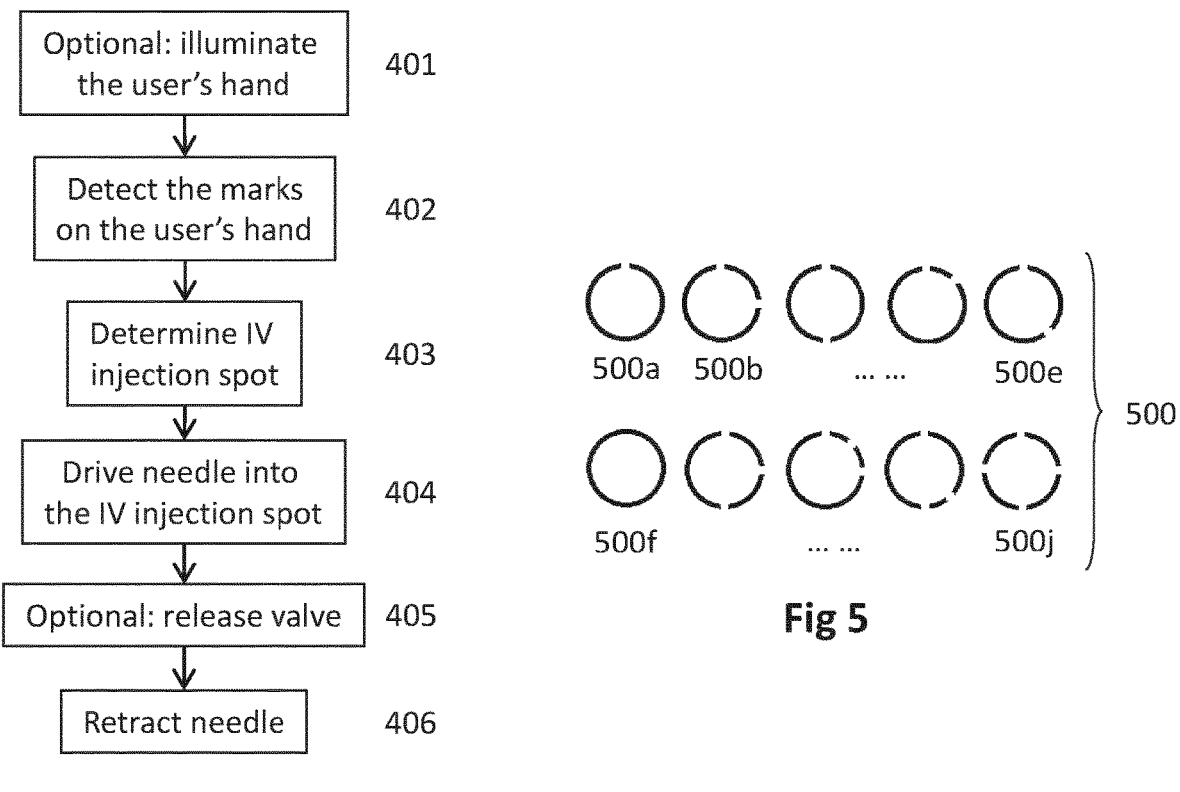
| | |
|---|---|
| Optional: illuminate the user's hand | 401 |
| Detect the marks on the user's hand | 402 |
| Determine IV injection spot | 403 |
| Drive needle into the IV injection spot | 404 |
| Optional: release valve | 405 |
| Retract needle | 406 |
Fig 4
500a    500b    ... ...    500e
500f    ... ...    500j    } 500
Fig 5
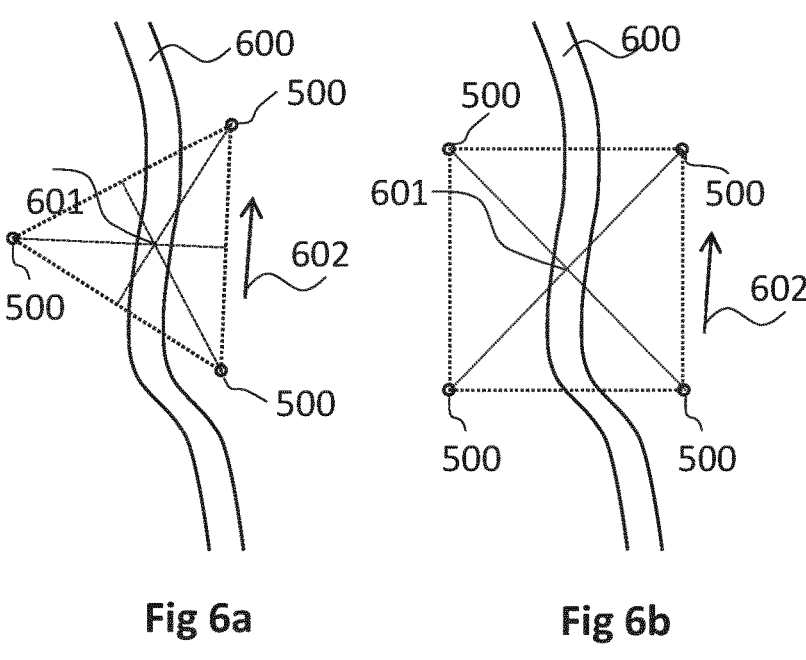
Fig 6a          Fig 6b

DEVICE AND PROCEDURE FOR SELF-INJECTION AND INSERTION OF NEEDLES OR CATHETERS INTRAVENOUSLY

CROSS REFERENCE TO RELATED APPLICATIONS

The present application is the national stage entry of International Patent Application No. PCT/EP2022/066852, filed on Jun. 21, 2022, and claims priority to Application No. EP 21315102.0, filed on Jun. 23, 2021, the disclosures of which are incorporated herein by reference.

TECHNICAL FIELD

The present disclosure relates to a device and procedure for self-injection and insertion of needles or catheters intravenously.

BACKGROUND

Not all medicaments that are administered by injection are suitable for subcutaneous administration. Certain diseases require intravenous (IV) administration of medicaments, i.e. administering the medicament into a vein. Conventionally, it is required that IV administration of a medicament is performed by a trained nurse (or other healthcare professional). This means that either the patient has to travel to a hospital or clinic, or the trained nurse has to travel to the patient's home. This brings additional costs to the patient, the hospital and the healthcare system.

Some fully automated IV injection systems and devices (i.e. devices that do not require any input from a trained nurse or other healthcare professional) may suffer from a number of drawbacks. Detecting veins using sensors may be unreliable; the devices may be expensive; and the users may be intimidated by a fully automated system, thus not complying with their therapy.

SUMMARY

Certain aspects of this disclosure relate to systems that can assist patients with IV administration of a medicament.

In a first aspect of the disclosure, a self-IV injection device is provided. The self-IV device comprises fixing means to fix the device with respect to a user's arm; an optical sensor; an IV needle; a drive; and a processor. The self-IV injection device is configured to: detect, using the optical sensor, positions of marks placed on the user's arm; based on the detected positions of marks placed on the user's arm, determine, using the processor, a suitable IV injection spot; and move the IV needle, using the drive, to the determined suitable IV injection spot such that the IV needle penetrates a user's vein.

In embodiments of the first aspect of the disclosure, one or more of the following features may be provided:

the device further comprises a light source to illuminate the user's skin and facilitate detection of the marks;

the drive is configured to drive the IV needle in a vertical direction and advance the IV needle forward;

the suitable IV injection spot is determined based on distances between the marks placed on the user's arm and the suitable IV spot, on angles between imaginary lines connecting the marks and the suitable IV injection spot, or on both the distances between the marks placed on the user's arm and the suitable IV spot and the angles between imaginary lines connecting the marks and the suitable IV injection spot;

the suitable IV injection spot is determined based on relative distances between the marks placed on the user's arm and the suitable IV spot, on relative angles between imaginary lines connecting the marks and the suitable IV injection spot, or on both the relative distances between the marks placed on the user's arm and the suitable IV spot and the relative angles between imaginary lines connecting the marks and the suitable IV injection spot;

the processor is further configured to recognize marks placed on the user's arm belonging to different groups corresponding to different suitable IV injection spots;

the processor is further configured to identify a particular user based on a unique design of the respective marks placed on the respective user's arm;

the device further comprised a valve operable by the processor to release a medicament into the needle;

the device is configured to identify more than one suitable self-IV injection spot, and determine a suitable self-IV injection spot based on an order in which the spots are to be used and information on history of use of the spots.

In a second aspect of the disclosure, a method of operating a self-IV injection device is provided. The device comprises fixing means to fix the device with respect to a user's arm; an optical sensor; an IV needle; a drive; and a processor. The method comprises detecting, using the optical sensor, positions of marks placed on the user's arm; based on the detected positions of marks placed on the user's arm, determining, using the processor, a suitable IV injection spot; and moving the IV needle, using the drive, to the determined suitable IV injection spot such that the IV needle penetrates a user's vein.

In a third aspect of the disclosure, a system is provided. The system comprises a device as described in connection with the first aspect of the disclosure, and a positioning aid, wherein the positioning aid is configured to be used to place the marks on user's hand.

In a fourth aspect of the disclosure, a method of operating a self-IV injection device is provided. The device comprises fixing means to fix the device with respect to a user's arm; an optical sensor; an IV needle; a drive; and a processor, The method comprises detecting, with the sensor, positions of marks placed previously on the user's arm; processing the detected marks to determine a suitable IV injection spot; moving the IV needle of the self-IV injection device to the determined suitable IV injection spot; and penetrating a user's vein at the suitable IV injection spot with the IV needle.

BRIEF DESCRIPTION OF THE DRAWINGS

The following description is with reference to the following Figures:

FIGS. 1a to 1d show a schematic view of a self-IV injection device in use.

FIG. 4 is a flow-chart illustrating the use of the self-IV injection device.

FIG. 5 is a schematic illustration of marks that may be used by the self-IV injection device.

FIGS. 6a and 6b show an example way of determining a suitable IV injection spot using the marks.

DETAILED DESCRIPTION

Figure 2:
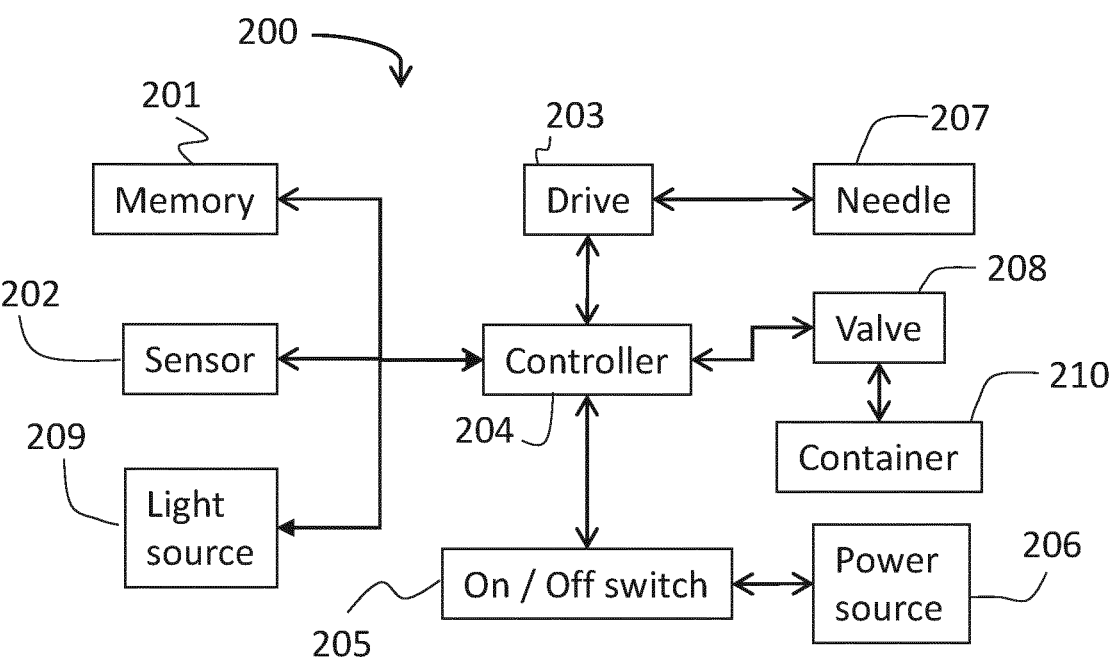
FIG. 2 is a schematic view of a self-IV injection device.

The Figures show examples of a self-IV injection device, and examples of how the self-IV injection device operates. The skilled person will appreciate that elements of different Figures and different embodiments described below can be combined as appropriate. The skilled person will also appreciate that many elements and features of the embodiments described below are optional. FIG. 2 is a schematic view of an example self-IV injection device 200 according to the present disclosure. The self-IV injection device 200 has a controller 204. The controller 204 determines the position of the device 200 with respect to a user's arm (as described below), and operates a drive 203. The self-IV injection device 200 further has a needle 207 that can penetrate the user's skin and vein. The needle 207 is connected to a drive 203 which is provided to move the needle 207. The self-IV injection device 200 further has a sensor 202 connected to the controller 204 and configured to detect marks 500 on the user's hand or forearm (described below), an on/off switch 205, a power source 206, a valve 208 regulating the flow of a medicament from a medicament container 210 into the needle 207, and a memory 201 storing instructions on operating the sensor 202, the drive 203 and optionally the valve 208.

The needle 207 may be any needle suitable for insertion into a vein. The needle 207 may also come with a cannula. The needle 207 may serve for insertion of a catheter.

The sensor 202 may be, for example, an optical sensor. The sensor 202 may be a photodetector, a charge-coupled device, a camera, or any other suitable device capable of detecting marks 500 on user's skin. Although the word 'sensor' is used in singular here, it will be understood that there may be multiple sensors in place of the sensor 202.

A light source 209 may be provided to illuminate the user's skin and facilitate detection of the marks 500 on the user's skin by the sensor 202. The light source 209 may provide visible light (about 380 nm to about 750 nm) to assist detection of the marks 500 in dark or otherwise suboptimal lighting conditions. Alternatively or in addition, the light source 209 may provide light of a specific wavelength/spectrum to illuminate marks that are less visible or invisible under visible light. For example, the light source 209 may provide UV light, IR light, light of specific colour, and the like.

The drive 203 is provided to move the needle 207. The needle 207 may be movable in a vertical direction ("up" and "down"). The needle 207 may be movable in a direction determined by the longitudinal axis of the needle ("forward" and "back"). The needle 207 may be movable to adjust horizontal and/or vertical angle between the needle 207 and the user's skin.

Figure 3:
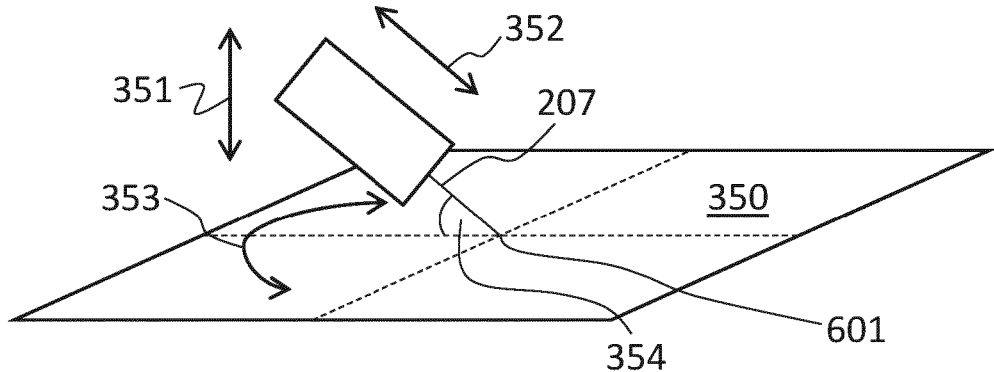
FIG. 3 is a schematic view of the degrees of freedom the self-IV injection device.

FIG. 3 illustrates the directions in which the drive 203 may drive the needle 207. For clarity, most components of the self-IV injection device 200 are omitted in FIG. 3. Initially, the needle is fixed under an angle 354 with respect to the user's skin 350. The angle 354 may be between 10 degrees and 40 degrees.

The drive 203 drives the needle 207 in a vertical direction ("up" and "down"), as illustrated by arrow 351. This "up" and "down" movement allows the needle 207 to reach the suitable IV injection spot 601 and retract as appropriate. The drive 203 also drives the needle 207 "forward" and "back", as illustrated by arrow 352. This movement allows the needle 207 to be inserted into the vein and retracted as appropriate. In addition, to improve precision, the drive 203 may adapt the horizontal angle of the needle 207 ("azimuth"), illustrated by arrow 353, the vertical angle of the needle 207 ("elevation"), i.e. change the angle 354, or both the horizontal angle and the vertical angle. If a less complex device is desired (e.g., due to lower cost and/or lower maintenance), the possibility to adapt the horizontal angle and/or the vertical angle ("azimuth" and/or "elevation") may be omitted.

The self-IV injection device 200 identifies the suitable IV injection spot 601 by identifying marks 500 placed on the user's skin. The known (pre-set and/or pre-stored) relationship between the marks 500 and the suitable IV injection spot 601 may then be used to determine the suitable IV injection spot. The known relationship between the marks 500 and the suitable IV injection spot 601 may be, e.g., distances between the marks 500 and the suitable IV injection spot 601, relative distances or ratios of distances between the marks 500 and the suitable IV injection spot 601, angles between imaginary lines connecting the marks 500 and the suitable IV injection spot 601 etc. Once a suitable IV injection spot 601 is identified, the needle 207 may be driven vertically down towards the suitable IV injection spot 601. As soon as the needle reaches the suitable IV injection spot 601, the needle 207 may be driven forward into the vein at the suitable IV injection spot 601.

The marks 500 are usually placed on the user's skin in advance, before the first IV injection takes place. An example process of placing the marks on the user's skin is shown in FIGS. 1a-d. In the example of FIGS. 1a-d, a positioning aid 100 is used. The use of the positioning aid 100 is however not critical. The positioning aid may have an aiming cross 101 and a number of positioning marks 102. The illustrated example shows three positioning marks 102, but there may be four or five positioning marks 102, or any other suitable number.

Using the positioning aid 100, a trained nurse or other healthcare professional (referred to as 'nurse' below) identifies a suitable IV injection spot 601 on the user's hand or forearm suitable for IV injection. In other words, the nurse identifies one or more veins that could be used for insertion of the needle 207. The nurse places the positioning aid 100 on the user's forearm such that the aiming cross 101 is positioned on the identified suitable IV injection spot 601. The nurse then creates marks 500 on user's skin, using the positioning marks 102. The marks 500 (described in more detail below) may be permanent or semi-permanent. For example, the marks 500 may be created using tattoo, any sort of permanent marker, and the like. The marks 500 may be created using a magnetic ink. The marks 500 may only be visible under light of a specific wavelength, e.g., UV or IR light. In some configurations, use of UV light may be advantageous.

Once a first set of marks 500 is created, the nurse may identify another spot on the user's hand suitable for insertion of a needle, and create a second set of marks 500. The second set of marks 500 may differ from the first set of marks 500 in design, colour, or other characteristic. This process may be repeated until a suitable number of sets of marks 500 is created, e.g., three, four, five, seven, ten or twelve sets of marks 500, to identify multiple spots on the user's arm.

The marks 500, positioned using a positioning aid 100, are placed in a precise position with respect to the suitable IV injection spot 601. This provides a standardized set of marks 500 that have the same relationship between the marks 500 and the suitable IV injection spot 601 for all users. This may enable the self-IV injection device 200 to store the same positioning information for all users, and thus the self-IV injection device 200 may be used by multiple users. This may be advantageous whenever more than one user needs a regular IV injection.

Alternatively or in addition, a predetermined number of marks 500 may be placed in spots on the user's hand or forearm without the use of the positioning aid 100. For example, the marks 500 may be placed in a predetermined relation to prominent points on the user's hand and/or forearm, such as elbow, elbow crease, wrist, and the like. The marks 500 may be placed in a predetermined relation to a suitable IV spot 601. The marks 500 may be placed in random locations on the user's hand and/or forearm. In some embodiments, the precise positioning of the marks 500 on the user's hand and/or forearm may not be critical, and the marks 500 may be placed "close to" a predetermined spot (e.g., on the anterior side of the forearm, in one third of the distance between the elbow and the wrist on the inner side) but precision may not be required. In such cases, the marks 500 may be placed within several centimetres of a preferred spot.

To utilize the marks 500 that are placed without positioning aid 100 (or more generally without precise positioning with respect to the suitable IV injection spot 601), the self-IV injection device 200 may detect the marks 500 and save the configuration of the marks 500 and the relationship between the marks 500 and suitable spots for IV injection for a specific user into its memory. The saved information may then be used to identify a suitable IV injection spot 601 for the specific user. In this way, the self-IV injection device 200 may create an image of the specific user or users before the self-IV injection device 200 is used for the first time.

In an embodiment, the memory 201 may store information on relative positions of the marks 500 rather than absolute distances between the marks 500. This may be advantageous in case the user gains or loses weight, as the relative distances between the marks are not likely to change even if the absolute distances change.

The self-IV injection device 200 detects and recognizes the marks 500. If more than one set of marks 500 is provided, the self-IV injection device 200 may be configured to recognize and distinguish marks 500 from different sets, and pick up marks 500 from a single set. Based on the recognition of the marks 500 and their positions, the self-IV injection device 200 identifies a suitable IV injection spot 601. Once the spot 601 is identified, the drive 203 may drive the needle down along the arrow 351 (FIG. 3) until the needle 207 reaches the user's skin, and then drive the needle 207 forward along the arrow 352 (FIG. 3) into the user's vein. When the injection is completed, the needle 207 may be retracted along the arrow 352 and then lifted along the arrow 351.

An example use of the self-IV injection device 200 is illustrated schematically in FIG. 4. Before use, the user's arm is preferably fixed with respect to the self-IV injection device 200 such that the user's wrist and their upper arm are fixed, the elbow is straightened, and the anterior of the user's forearm, which carries the marks 500, is exposed to the sensor 202 and the needle 207. In an embodiment, the self-IV injection device 200 may itself fix to the user's arm, e.g., at wrist and upper arm. In some embodiments, it may be advantageous to prevent the user's arm from moving and/or bending.

The controller 204 uses the sensor 202 to detect the marks 500 (step 402). Depending on the type of self-IV injection device 200, if the visibility is poor and/or if the marks are only visible using a specific wavelength, the controller 204 may use the light source 209 to illuminate the user's hand during detection (step 401). Based on the position of the marks 500, the controller 204 identifies a suitable IV injection spot 601 (step 403). The controller 204 operates the drive 203 to insert the needle 207 into the user's vein, as described above (step 404). Depending on the type of self-IV injection device 200, the controller 204 may operate the valve 208 to facilitate transfer of medicament from a medicament storage (e.g., a medicament container 210, a medicament bag and the like) to the needle 207 and thus to the user's vein (step 405). Alternatively or in addition, the user or their caretaker may release the valve 208 by hand. Once the delivery of the medicament is completed, the needle 207 is retracted, as described above (step 406).

Insertion of the IV injection normally has a limited range of suitable insertion angles. The insertion angle 354 may be, e.g., between 15 degrees and 35 degrees.

To assist the sensor 202 and the controller 204 in detecting the marks 500 and/or distinguishing marks from different sets and/or determining a suitable IV injection spot 601, each mark 500 may be provided with a unique design. An example is shown in FIG. 5. In this example, marks 500a to 500j are each provided with a different design; this may be used to distinguish the marks 500a to 500j from each other and/or encode other information. It will be appreciated that FIG. 5 is provided for illustration purposes only. There may be more unique designs than 10, the unique designs could be based on any other shape than circle, the unique design may be based on more than one shape (e.g., a combination of different shapes), the design of each mark 500 may be simpler or more complex (e.g., to allow encoding more complex information), and the like, as appropriate. It will also be appreciated that not each of the marks 500 may be provided with unique design. For example, marks 500 in a single group may have the same or corresponding design; using the example of FIG. 5, there may be a set of marks with the design 500a, a set of marks with the design shown in 500b, etc. For example, a group of marks 500 may correspond to one suitable IV injection spot 601, and the marks from this group may be all provided with the same design, distinct from the design of any other group. Alternatively or in addition, only some marks 500 may be provided with a unique design, e.g., those in certain prominent locations. The memory 201 of the device 200 then stores information encoded in the design of the marks 500 (e.g., their grouping, their prominent positions, and the like, as described above).

The controller 204 has access to information stored in memory 201. The information stored may be on positioning of each mark 500. Positioning of marks 500 may be based on, e.g., known distances between the marks 500, known angles between imaginary lines connecting the marks 500, the distances to prominent points on user's hand and/or forearm, relative distances between the marks 500, relative angles between imaginary lines connecting the marks 500, and the like. In case the marks 500 are provided with unique design as described above, information on the design may be stored in addition to information on the positioning of the marks 500.

The unique design of the marks 500 may be used to identify a specific user to the self-IV injection device 200. Alternatively or in addition, other ways of identification of a specific user may be used. Identifying a specific user may be advantageous in cases where the same self-IV device is used by more than one user.

FIGS. 6a and 6b show two examples of how a suitable IV injection spot 601 can be identified. The self-IV injection device 200 identifies the marks 500. FIG. 6a shows the marks 500 arranged in a triangle; FIG. 6b shows the marks 500 arranged in a square. With more than three points, other arrangements than a square may be used, e.g., a rectangle or a trapezoid. More than four points may be used to identify the suitable IV injection spot 601, e.g., 6 points (not shown).

In the examples shown in FIGS. 6a and 6b, the marks 500 are arranged along (next to) a vein 600, in the vicinity of a suitable IV injection spot 601. The self-IV injection device 200 detects the marks 500 using sensor 202, as described above. The relative positions of the marks 500 and the suitable IV injection spot 601 are known and stored in memory 201. The self-IV injection device 200 may thus use the detected positions of the marks 500 to determine the position of the suitable IV injection spot 601. In addition, based on the detected positions of the marks 500, the self-IV injection device 200 may determine a direction 602 from which the needle 207 approaches the suitable IV injection spot 601 (i.e. the angle 353 shown in FIG. 3.

The information on the relative positions of marks 500 and the suitable IV injection spot or spots 601 is stored in the memory 201 of the self-IV injection device 200. This information may be unique for each user (i.e. the self-IV injection device 200 may be personalized for each user). In such case, the information is stored in the memory 201 of the self-IV injection device 200 during its first, nurse-supervised use. For example, the nurse may identify one or more of suitable IV injection spots 601 and guide the self-IV injection device 200 in detecting and storing the relative positions of the marks 500 and the suitable IV injection spot(s) 601. The subsequent procedure may be as described above.

Identifying and providing marks 500 for more than one suitable IV injection spot 601 may be advantageous. In certain situations, repeated IV injections to exactly the same spot may cause scarring or vein inflammation. This may be problem especially for haemophiliac patients. By identifying and using several suitable IV injection spots 601, the time interval between injecting into the same spot may be increased, thus lowering the risk of adverse effects to the user.

For example, there may be 8 suitable IV injection spots 601 identified on user's arms. Depending on several factors, the self-IV injection device 200 may store information about which suitable IV injection spot 601 is to be injected when the next injection is due. For example, based on one or more of the proximity of the suitable self-IV spots to each other, the information on which spot has been used last time, the order in which the spots should be used, and other factors, the self-IV injection device may determine the spot to be used in the next injection. For example, numbering the spots consecutively 1 to 8, the order of the spots may be 1-2-3-4-5-6-7-8, 1-3-5-7-2-4-6-8, 1-5-2-7-8-3-4-6, or any other suitable order. This order may be pre-set by a nurse before the first use of the self-IV injection device 200.

The self-IV injection device 200 may be provided with a medicament container 210. A medicament container 210 may be connectable to the self-IV injection device 200. The medicament container 210 is connected to and in fluid communication with the needle 207. Any suitable means for connecting the container 210 to the needle 207 may be used, e.g., a flexible plastic tube. The medicament container 210 may be connected to the needle 207 via a valve 208, which by opening, closing and/or partially closing may regulate the flow of the medicament to the needle 207 and into the user's vein. The valve 208 may be operated by the processor or controller 204. Alternatively or in addition, the valve 208 may be operated by the user.

The valve 208 may enable a linear flow of the medicament to the needle 207. Alternatively or in addition, the valve 208 may enable different profiles of flow of the medicament to the needle 207. For example, the flow may be slow in the initial phase of the medicament administration, ramping up and reaching a maximum flow in the second phase of the medicament administration, and slowing down to zero in a third phase of medicament administration. Other suitable profiles of the flow rate are possible. The profile of the flow rate may be determined based on the medicament administered and the user's medical condition.

The self-IV injection device as described above may be advantageous for patients suffering from a number of diseases or conditions that require regular IV administration of medicaments. For example, the self-IV injection device may be used by patients suffering from rare diseases, oncology patients, haemophilia patients, or patients that require regular blood tests.

The self-IV injection device saves time of a healthcare professional, and thus also the costs to the healthcare system. The self-IV injection device may be used in the user's home, but also in hospitals, care homes or research.

The user of the self-IV injection device may store the medicament used for the IV administration at home, e.g., in their fridge. The patient may be trained in inserting a fresh medicament container 210 each time administration of the medicament is required.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber May be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks 10) such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino 30 acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); 10) B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems, and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A self-IV injection device comprising:
   a member configured to fix the device with respect to an arm of a user;
   an optical sensor;
   an IV needle;
   a drive; and
   a processor;
   wherein the self-IV injection device is configured to:
      detect, using the optical sensor, positions of marks placed on the arm of the user;
      determine, using the processor and based on the detected positions of marks placed on the arm of the user, a suitable IV injection spot; and
      move the IV needle, using the drive, to the determined suitable IV injection spot such that the IV needle penetrates a vein of the user.

2. The self-IV injection device of claim 1, wherein the device further comprises a light source configured to illuminate skin of the user and facilitate detection of the marks.

3. The self-IV injection device of claim 2, wherein the optical sensor comprises a photodetector, a charge-coupled device, or a camera.

4. The self-IV injection device of claim 2, wherein the drive is configured to drive the IV needle in a vertical direction relative to the user and advance the IV needle forward along a longitudinal axis of the IV needle.

5. The self-IV injection device of claim 2, wherein the suitable IV injection spot is determined based on distances between the marks placed on the arm of the user and the suitable IV spot, on angles between imaginary lines connecting the marks and the suitable IV injection spot, or on both the distances between the marks placed on the arm of the user and the suitable IV spot and the angles between imaginary lines connecting the marks and the suitable IV injection spot.

6. The self-IV injection device of claim 5, wherein the suitable IV injection spot is determined based on relative distances between the marks placed on the arm of the user and the suitable IV spot, on relative angles between imaginary lines connecting the marks and the suitable IV injection spot, or on both the relative distances between the marks placed on the arm of the user and the suitable IV spot and the relative angles between imaginary lines connecting the marks and the suitable IV injection spot.

7. The self-IV injection device of claim 2, wherein the processor is further configured to recognize marks placed on the arm of the user belonging to different groups corresponding to different suitable IV injection spots.

8. The self-IV injection device of claim 7, wherein the processor is further configured to identify a particular user based on a unique design of the respective marks placed on the respective user's arm.

9. The self-IV injection device of claim 7, wherein the device is configured to identify more than one suitable self-IV injection spot, and determine a suitable self-IV injection spot based on an order in which the spots are to be used and information on history of use of the spots.

10. The self-IV injection device of claim 1, wherein the drive is configured to drive the IV needle in a vertical direction relative to the user and advance the IV needle forward along a longitudinal axis of the IV needle.

11. The self-IV injection device of claim 10, wherein the device further comprises a valve operable by the processor to release a medicament into the needle.

12. The self-IV injection device of claim 1, wherein the suitable IV injection spot is determined based on distances between the marks placed on the arm of the user and the suitable IV spot, on angles between imaginary lines connecting the marks and the suitable IV injection spot, or on both the distances between the marks placed on the arm of the user and the suitable IV spot and the angles between imaginary lines connecting the marks and the suitable IV injection spot.

13. The self-IV injection device of claim 1, wherein the suitable IV injection spot is determined based on relative distances between the marks placed on the arm of the user and the suitable IV spot, on relative angles between imaginary lines connecting the marks and the suitable IV injection spot, or on both the relative distances between the marks placed on the arm of the user and the suitable IV spot and the relative angles between imaginary lines connecting the marks and the suitable IV injection spot.

14. The self-IV injection device of claim 1, wherein the processor is further configured to recognize marks placed on the arm of the user belonging to different groups corresponding to different suitable IV injection spots.

15. The self-IV injection device of claim 1, wherein the processor is further configured to identify a particular user based on a unique design of the respective marks placed on the respective user's arm.

16. The self-IV injection device of claim 1, wherein the device further comprises a valve operable by the processor to release a medicament into the needle.

17. The self-IV injection device of claim 1, wherein the device is configured to identify more than one suitable self-IV injection spot, and determine a suitable self-IV injection spot based on an order in which the spots are to be used and information on history of use of the spots.

18. The self-IV injection device of claim 1, wherein the optical sensor comprises a photodetector, a charge-coupled device, or a camera.

19. A method of operating a self-IV injection device, the device comprising a member configured to fix the device with respect to an arm of a user; an optical sensor; an IV needle; a drive; and a processor, the method comprising:

detecting, using the optical sensor, positions of marks placed on the arm of the user;

based on the detected positions of marks placed on the arm of the user, determining, using the processor, a suitable IV injection spot; and moving the IV needle, using the drive, to the determined suitable IV injection spot such that the IV needle penetrates a vein of the user.

20. A system comprising:

a self-IV injection device comprising:

a member configured to fix the device with respect to an arm of a user;

an optical sensor;

an IV needle;

a drive; and a processor;

wherein the self-IV injection device is configured to:

detect, using the optical sensor, positions of marks placed on the arm of the user;

determine, using the processor and based on the detected positions of marks placed on the arm of the user, a suitable IV injection spot; and move the IV needle, using the drive, to the determined suitable IV injection spot such that the IV needle penetrates a vein of the user; and a positioning aid, wherein the positioning aid is configured to be used to place the marks on a hand of the user.

\* \* \* \* \*